United States Patent
Hager

[11] 4,061,500
[45] Dec. 6, 1977

[54] PRESERVATIVE FOR WOOD AND OTHER FIBROUS MATERIALS

[76] Inventor: Bror Olof Hager, Forsetevagen 5, Djursholm, Sweden

[21] Appl. No.: 703,287

[22] Filed: July 7, 1976

[30] Foreign Application Priority Data

Mar. 29, 1974 Sweden .................................. 7404296

[51] Int. Cl.² ............................................... C09D 5/14
[52] U.S. Cl. ..................................... 106/15 R; 106/18; 106/243; 252/109; 424/317; 424/318; 427/440
[58] Field of Search ............. 424/317, 318; 106/15 R, 106/18, 243; 252/108, 109; 427/440

[56] References Cited

U.S. PATENT DOCUMENTS

| | | | |
|---|---|---|---|
| 1,809,470 | 6/1931 | Budowski | 106/243 |
| 2,190,714 | 2/1940 | Hoffman et al. | 424/317 |
| 3,564,098 | 2/1971 | Erwin et al. | 424/317 |

*Primary Examiner*—Lorenzo B. Hayes
*Attorney, Agent, or Firm*—Burns, Doane, Swecker & Mathis

[57] ABSTRACT

A wood preservative effective against blue stain containing a fatty acid of 6-11 carbon atoms, boric acid and an alkali compound in stoichiometric excess of the fatty acid. The resulting composition is readily soluble in water, and the resulting solution can be applied by spraying onto the wood or be used as a bath into which wood is dipped.

4 Claims, No Drawings

PRESERVATIVE FOR WOOD AND OTHER FIBROUS MATERIALS

The present invention relates to preservatives against blue stain on wood and other fibrous organic materials.

As described in my U.S. patent application Ser. No. 218,546, some fatty acids have a higher effect against wood-destroying fungi. The degree of preservative effect follows a certain pattern. From acetic acid, with its two carbon atoms, the effect of the acids increases with higher number of carbon atoms and gradually the effect becomes very high. This continues up to the fatty acid with 11 carbon atoms. There the pattern is broken. The fatty acid with 12 carbon atoms has lower preserving effect than the previous acid in the series. The acids with 13 or more carbon atoms seem to have very little or no preserving effect. With higher number carbon atoms the acids become more and more difficultly soluble, which circumstance suggests that the failing effect of the acids with more than 12 carbon atoms depends from the fact that they are too difficultly soluble.

The effective acids can be obtained at comparatively low prices, — at least this is valid for the acids with an even number of carbon atoms, for instance the caproic, caprylic and capric acids which contain 6-8-10 carbon atoms, respectively. The acids have been used for pressure impregnation of wood in combination with copper, according to the above-identified patent application.

As the present invention is concerned with the protection of wood against blue stain, it is desirable to avoid metal components because they as a rule do not give real advantage. For the purpose in question the effect of metal component is not specially high, and their very high fixation of the acids is not needed. They make the preservative more expensive. In other cases, presence of metals occasions disadvantages such as discoloring of the wood, wear of wood-working tools and trouble at a later adaption of the wood.

The said acids have good properties as blue stain preservatives. They can be dissolved in organic solvents and be applied to the wood in the form of such a solution. After the treatment, the solvent evaporates while the protecting acid remains in the wood. However, for practical purposes use of those solvents may not be suitable. In the first place, they are expensive; they may occasion health problems, and furthermore they may constitute fire risks.

Emulsions of the acids can also be made up but only with difficulties; these emulsions are not so easy to use.

Aqueous solutions of the acids are to be preferred as these are simpler and more effective to use and further they are cheaper. The present invention has solved the problem to manufacture preservatives of the acids easy soluble in water.

The dissolution of the fatty acids in water must be carried out in a special way.

The first way to consider is to dissolve the acids with the help of alkali hydroxide. This way does, however, not give a good solution of the problem. To neutralize the acid with alkali hydroxide to a neutral salt does not give a product easy to dissolve in water. A surplus of alkali also gives trouble and products not suitable for distribution are obtained. To illustrate the situation the following experiments can be related.

To 100 ml of water 2 grams of caprylic acid was added together with different amounts of KOH. The following results were noted:

Table 1

| Amount KOH added | Appearance of mixture | |
|---|---|---|
| 0.78 grams | heavy unstable emulsion | pH 8 |
| 1.5 | heavy flocculation | pH over 12 |
| 3.0 | heavy flocculation | " |
| 6.0 | light flocculation | " |
| 12.0 | clear solution | " |

The amounts of KOH added correspond to 1, 2, 4, 8 and 16 equivalents of the 2 grams of caprylic acid used.

The same experiments were carried out with sodium hydroxide and ammonia instead of potassium hydroxide. Better dissolution of the caprylic acid was not obtained.

Of the results obtained it is clear that reasonable amounts of alkali hydroxide do not solve the problem to give a product suitable for dissolution in water and application on wood. High amounts of strong alkali are not easy to handle; they do not give products suitable for distribution, and they yield expensive products.

After different tests it seems clear that the problem to obtain good water solutions depends on a certain alkalinity and on the presence of some amounts of electrolytes. The most suitable alkalinity seems according to applicant's test, to be around pH 10.5. This level can be obtained in an easy way by using alkali carbonate as a dissolving agent which will give a suitable alkalinity at the same time as it will give the needed electrolytes.

To illustrate this the following tests can be related:

To 100 ml of water 2 grams of caprylic acid was added together with different amounts of $Na_2CO_3$. The following results were noted:

Table 2

| Amount $Na_2CO_3$ added | Appearance of mixture | |
|---|---|---|
| 0.74 grams | heavy unstable emulsion | pH 6.8 |
| 1.5 | flocculation | 9.5 |
| 3.0 | very light flocculation | 10.0 |
| 6.0 | clear solution | 10.5 |
| 12.0 | clear solution | 10.5 |

The amounts of $Na_2CO_3$ added correspond to 1, 2, 4, 8 and 16 equivalents of the 2 grams of caprylic acid used.

A third test to illustrate the situation can be given. To 100 ml of water 2 grams of caprylic acid was added and dissolved with the help of 3 grams $Na_2CO_3$ — the smallest possible amount necessary for obtaining solution. Then different amounts of KOH were added.

Table 3

| Amounts KOH added | Appearance of mixture | |
|---|---|---|
| 0 grams | solution (very light flocculation) | pH 10 |
| 1 | heavy emulsion, not stable | 12 |
| 2 | light flocculation | 12 |
| 4 | light flocculation | >12 |
| 8 | very light flocculation | >12 |
| 16 | clear solution | >12 |

From this test it is clear that an increase of the pH increases the difficulties of obtaining dissolution. For the high pH a very high surplus of chemicals is necessary for obtaining dissolution.

Another question is to have a mixture suitable for distribution and handling. Best is to have a powder, while a paste may also be acceptable but a two-phase system with a high alkali content is not recommended.

Suitable preservative products easy to handle, distribute and dissolve, can be obtained by reacting one or another of the acids with alkali carbonate. The amount of carbonate has to be larger than the equivalent amount of acid, — i.e. the carbonate shall according to the above tests be used in at least 4 times stoichiometric excess in view of the fatty acids. By the reaction some carbon dioxide is developed and a ready-to-use product is formed. It is easy to handle and can be dissolved in water and used for the intended purpose. Acids with 8 carbon atoms or less give clear colorless solutions; as a rule, acids with a higher number of carbon atoms give opalescent solutions.

A preservative based on alkali carbonate can be produced by mixing (reacting):

EXAMPLE 1

30 parts of caprylic acid (and/or other fatty acid)
45 parts or more of sodium carbonate, $Na_2CO_3$
Composition figures here and below are given in parts by weight.

Instead of mixing the acids exclusively with carbonate, they can be mixed with some alkali — sodium or potassium hydroxide — and some carbonate.

Such preservative can be produced by mixing:

EXAMPLE 2

30 parts caprylic acid
30 parts $Na_2CO_3$
5 parts KOH

This represents a very good way to product the preservative. The surplus of alkali compounds can here be a little reduced. In the given example alkali compounds are used to about 3½ equivalents of the amount of the fatty acid. An easy to handle powder is produced.

The aforesaid acids can be used in combination with other active agents for instance: formaldehyde; sorbic, benzoic salicylic and/or propionic acid. Inorganic compounds as boric acid can also be included. Here a synergetic effect may be observed, i.e. the rule that two (or several) different preserving agents mixed often give higher effect than the sum of the effects of the agents.

In the case formaldehyde is added, it can be introduced in the form of solid paraformaldehyde.

As the preservative mixtures represent a buffered system, the mixtures can very suitably be produced from substances having such properties. As some such substances are active agents these are specially adapted for the purpose. As an example of such compound boric acid can be named. Further it can be said that such substances can replace the carbonate as electrolyte. A mixture with high boric acid content is the following:

EXAMPLE 3

30 parts caprylic acid
50 parts boric acid, $H_3BO_3$
50 parts KOH

In order to complete the description of the invention the following examples are given. according to An effective protection against blue stain is obtained if the wood is sprayed with or dipped in a 6 percent water solution of the preservatives according to any one of the Examples 1–5.

For the treatment of wood 6 percent water solutions of the products according to Examples 2 and 3 were made up.

For protecting the wood to be treated against blue stain one part of wood was dipped in the Example 2 water solution and a second part of wood was dipped in the Example 3 solution during a period of 2 minutes. The treated wood samples were found not to be attacked by blue stain when subjected to conditions promoting attack by blue stain in comparison samples of wood not treated.

I claim:

1. An alkaline-reacting preservative composition for protection of wood against blue stain consisting of,
    a normal fatty acid having from 6 to 11 carbon atoms;
    boric acid; and
    at least one alkaline compound selected from the group consisting of sodium hydroxide, sodium carbonate, potassium hydroxide and potassium carbonate,
    the amount of said alkaline compound present being in a stoichiometric surplus based on the fatty acids and sufficient to make the preservative composition freely soluble in water.

2. Preservative composition according to claim 1, wherein the alkaline compound is sodium carbonate or potassium carbonate and the stoichiometric surplus of alkaline compound in view of the acids is at least 4 times.

3. Preservative composition according to claim 1, wherein the pH of a water solution of the preservative composition is approximately 10.5.

4. Preservative composition according to claim 1, further characterized in that it approximately consists of 30 parts caprylic acid, 50 parts boric acid and 50 parts potassium hydroxide.

* * * * *